United States Patent
Smith et al.

(10) Patent No.: US 9,166,321 B2
(45) Date of Patent: Oct. 20, 2015

(54) THIN PROFILE STACKED LAYER CONTACT

(75) Inventors: Alexander K. Smith, Chesterland, OH (US); Daniel N. Kelsch, Fairview Park, OH (US)

(73) Assignee: GREATBATCH LTD., Clarence, NY (US)

( * ) Notice: Subject to any disclaimer, the term of this patent is extended or adjusted under 35 U.S.C. 154(b) by 733 days.

(21) Appl. No.: 13/053,640

(22) Filed: Mar. 22, 2011

(65) Prior Publication Data

US 2012/0245664 A1   Sep. 27, 2012

(51) Int. Cl.
*A61N 1/375* (2006.01)
*H01R 13/11* (2006.01)
*H01R 24/58* (2011.01)

(52) U.S. Cl.
CPC ............ *H01R 13/111* (2013.01); *A61N 1/3752* (2013.01); *H01R 24/58* (2013.01); *H01R 2201/12* (2013.01)

(58) Field of Classification Search
CPC ..................................... A61N 1/3752
USPC ................................. 607/117, 119
See application file for complete search history.

(56) References Cited

U.S. PATENT DOCUMENTS

| | | | |
|---|---|---|---|
| 4,898,173 A * | 2/1990 | Daglow et al. | 607/37 |
| 5,417,714 A | 5/1995 | Levine et al. | |
| 5,730,628 A * | 3/1998 | Hawkins | 439/843 |
| 5,865,641 A | 2/1999 | Swart et al. | |
| 6,029,090 A | 2/2000 | Herbst | |
| 6,058,326 A | 5/2000 | Hess et al. | |
| 6,120,467 A | 9/2000 | Schallhorn | |
| 6,219,580 B1 | 4/2001 | Faltys et al. | |
| 6,393,316 B1 | 5/2002 | Gillberg et al. | |
| 6,505,077 B1 | 1/2003 | Kast et al. | |
| 6,622,048 B1 | 9/2003 | Mann et al. | |
| 6,625,488 B2 | 9/2003 | Poore et al. | |
| 6,659,968 B1 | 12/2003 | McClure | |
| 6,687,538 B1 | 2/2004 | Hrdlicka et al. | |
| 6,754,533 B1 | 6/2004 | Helfinstine et al. | |
| 6,892,098 B2 | 5/2005 | Ayal et al. | |

(Continued)

FOREIGN PATENT DOCUMENTS

| | | |
|---|---|---|
| DE | 101 34 277 A1 | 1/2003 |
| EP | 1995685 | 11/2008 |

(Continued)

OTHER PUBLICATIONS

Kataoka et al; "Contact Properties of Ni Micro-Springs for MEMS Probe Card", (2004) pp. 231-235.

(Continued)

*Primary Examiner* — Joseph Dietrich
(74) *Attorney, Agent, or Firm* — Pearne & Gordon LLP

(57) ABSTRACT

A connector is described herein that includes a plurality of layers patterned in two dimensions and joined in a stack with a bore there through. At least a subset of the plurality of layers are contact layers that include deflectable members (e.g., springs) that deflect in plane or out of plane upon insertion of a lead into the bore through the connector. The deflectable members form redundant electrical connections with the lead when the lead is inserted into the bore. For example, the connector can be incorporated into an implantable medical device (e.g., IPG). Moreover, methods of manufacturing a connector are set forth herein.

34 Claims, 10 Drawing Sheets

(56) References Cited

U.S. PATENT DOCUMENTS

| | | |
|---|---|---|
| 7,065,412 B2 | 6/2006 | Swoyer et al. |
| 7,177,691 B2 | 2/2007 | Meadows et al. |
| 7,187,976 B2 | 3/2007 | Duncan et al. |
| 7,236,822 B2 | 6/2007 | Dobak, III |
| 7,263,400 B2 | 8/2007 | Helfinstine et al. |
| 7,289,852 B2 | 10/2007 | Helfinstine et al. |
| 7,483,748 B2 | 1/2009 | Torgerson et al. |
| 7,493,159 B2 | 2/2009 | Hrdlicka et al. |
| 7,526,338 B1 | 4/2009 | Gill et al. |
| 7,551,964 B2 | 6/2009 | Dobak, III |
| 7,647,111 B2* | 1/2010 | Ries et al. ............... 607/37 |
| 7,680,540 B2 | 3/2010 | Jensen et al. |
| 7,702,385 B2 | 4/2010 | Moffitt et al. |
| 7,715,912 B2 | 5/2010 | Rezai et al. |
| 7,805,197 B2 | 9/2010 | Bradley |
| 7,813,809 B2 | 10/2010 | Strother et al. |
| 7,937,158 B2 | 5/2011 | Erickson et al. |
| 8,024,035 B2 | 9/2011 | Dobak, III |
| 8,190,259 B1 | 5/2012 | Smith et al. |
| 8,260,424 B2 | 9/2012 | Moffitt et al. |
| 8,495,640 B2 | 7/2013 | Krauss |
| 8,509,906 B2 | 8/2013 | Walker et al. |
| 8,571,677 B2 | 10/2013 | Torgerson et al. |
| 2003/0125773 A1 | 7/2003 | Havel et al. |
| 2003/0171685 A1 | 9/2003 | Lesser et al. |
| 2003/0204221 A1 | 10/2003 | Rodriguez et al. |
| 2003/0204224 A1 | 10/2003 | Torgerson et al. |
| 2003/0204225 A1 | 10/2003 | Heathershaw et al. |
| 2004/0098067 A1 | 5/2004 | Ohta et al. |
| 2005/0010625 A1 | 1/2005 | Andrews |
| 2005/0027325 A1* | 2/2005 | Lahti et al. ............... 607/37 |
| 2005/0179458 A1 | 8/2005 | Chen et al. |
| 2006/0259098 A1 | 11/2006 | Erickson |
| 2007/0078498 A1 | 4/2007 | Rezai et al. |
| 2007/0200576 A1 | 8/2007 | Laurent et al. |
| 2007/0213783 A1 | 9/2007 | Pless |
| 2008/0177351 A1 | 7/2008 | Fang et al. |
| 2009/0149917 A1 | 6/2009 | Whitehurst et al. |
| 2009/0256583 A1 | 10/2009 | Chen et al. |
| 2009/0265153 A1 | 10/2009 | Mazeau et al. |
| 2010/0063555 A1* | 3/2010 | Janzig et al. ............... 607/2 |
| 2011/0029040 A1 | 2/2011 | Walker et al. |
| 2011/0160810 A1 | 6/2011 | Griffith |
| 2011/0184496 A1 | 7/2011 | Kallmyer |
| 2011/0208265 A1 | 8/2011 | Erickson et al. |
| 2011/0270363 A1* | 11/2011 | Schramm et al. ............... 607/72 |
| 2012/0071951 A1 | 3/2012 | Swanson |
| 2012/0245664 A1 | 9/2012 | Smith et al. |
| 2012/0265272 A1 | 10/2012 | Judkins |
| 2013/0096641 A1 | 4/2013 | Strother et al. |
| 2013/0197615 A1 | 8/2013 | Rundle et al. |

FOREIGN PATENT DOCUMENTS

| | | |
|---|---|---|
| TW | 426868 B | 3/2001 |
| WO | 03090849 | 11/2003 |

OTHER PUBLICATIONS

Gwilliam, et al., Dept. of Bioengineering, University of Utah, "A Charge-balanced Pulse Generator for Nerve Stimulation Applications", http://www.sciencedirect.com, Publication date: Sep. 12, 2007.

Ji-Jon Sit Sarpeshkar, R., Massachusetts Inst. of Technol., Cambridge, "A Low-Power Blocking-capacitor-free Charge-balanced Electrode-stimulator Chip with less than 6 Na Dc Error for 1-ma Full-scale Stimulation", Publication Date: Sep. 2007, pp. 172-183.

Pawel Hottowy et al., "An integrated multichannel waveform generator for large-scale spatio-temporal stimulation of neural tissue", Analog Integrated Circuits and Signal Processing, Klumer Academic Publishers, BO, vol. 55, No. 3, Dec. 12, 2007, pp. 239-248, XP019598890, ISSN: 1573-1979, "the whole document".

Extended European Search Report; Date: Aug. 1, 2014; Reference: PT03149EP; Application No. 13186926.5-1652; Applicant: Greatbatch Ltd.; Place of Search: Munich; Date of Completion of Search: Dec. 20, 2013.

* cited by examiner

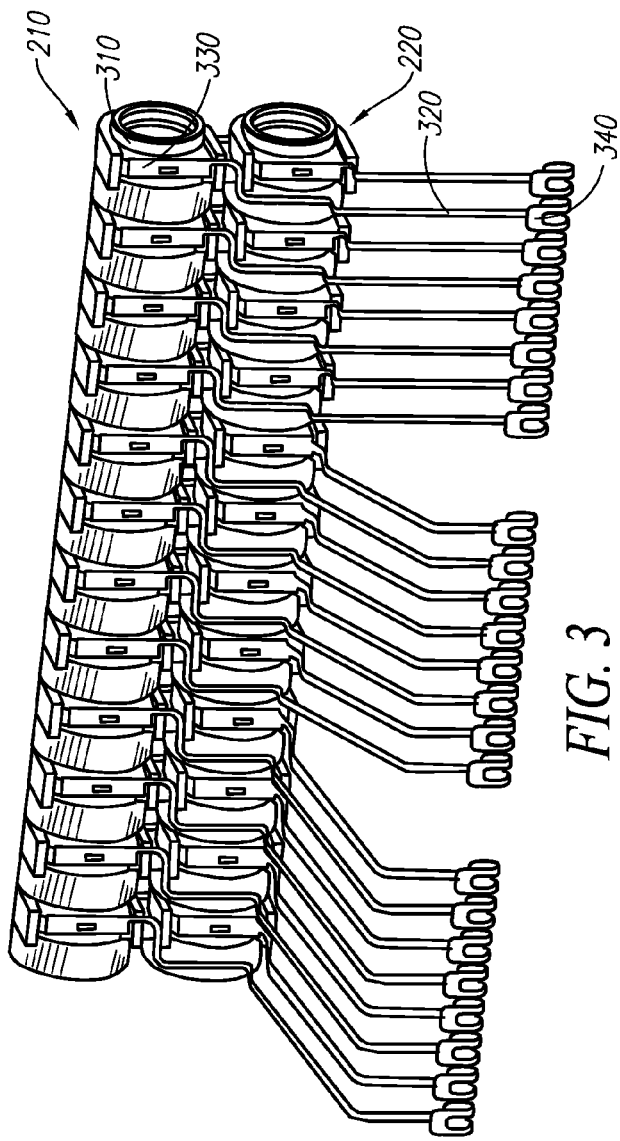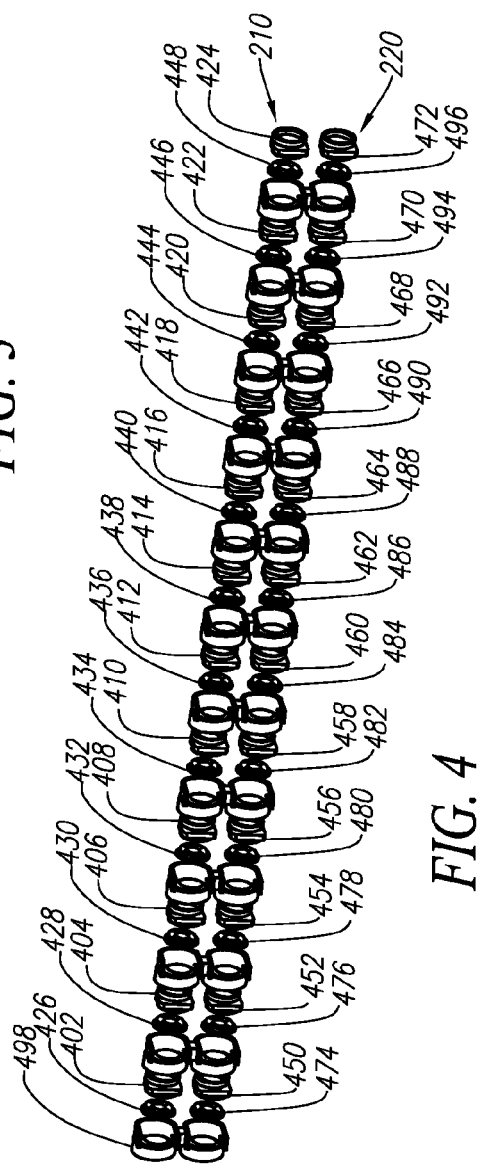
FIG. 3
FIG. 4

THIN PROFILE STACKED LAYER CONTACT

BACKGROUND

1. Field

This application relates generally to a connector for a medical device and, more specifically, to a connector with a plurality of layers patterned in two dimensions joined in a stack with at least one of the layers being a contact layer with deflectable members.

2. Background

Medical devices have been implanted in patients to perform a variety of tasks. For example, programmable pulse generating systems are used to treat chronic pain by providing electrical stimulation pulses from an epidural electrode array placed near a patient's spine. Such Spinal Cord Stimulation (SCS) is useful for reducing pain in certain populations of patients. SCS systems typically include one or more electrodes connected to one or more connectors of an External Pulse Generator (EPG) or an Implanted Pulse Generator (IPG) via leads. In the case of an EPG, the lead must be connected to the EPG via an exit from the body. The pulse generator, whether internal or external, generates pulses that are typically delivered to the dorsal column fibers within the spinal cord through the electrodes which are implanted along or near the dura of the spinal cord. In a typical situation, the attached leads exit the spinal cord and are tunneled around the torso of the patient to a subcutaneous pocket where the IPG is implanted, or the wires exit the patient for connection to the EPG.

Generally, smaller sized IPGs that incorporate increased numbers of contacts are being manufactured and employed in SCS systems. For instance, leads with a larger number of inline contacts having decreased pitches are being utilized with electrical connectors integrated into the IPGs. However, decreasing the size of IPGs and increasing the number of contacts incorporated into IPGs yields a packaging problem for the electrical connectors included in the IPGs. Moreover, reliability of forming a contact between the inline contacts of a lead and the corresponding respective contacts of the electrical connectors included in the IPGs is typically diminished with conventional electrical connectors as the size of the electrical connectors is decreased and the number of contacts of the electrical connectors is increased. Further, since a lead is oftentimes fairly limp, as the number of contacts of the electrical connector is increased, it can become more difficult to insert the lead without buckling of the lead.

A conventional electrical connector for IPGs incorporates a set screw that can be tightened on top of a ring to physically retain a lead inserted into such connector. Another conventional electrical connector incorporated in IPGs has a coiled spring inside a contact block. Ends of the spring are welded together yielding a torus shape through which a lead is inserted. The spring coils cant to conform to the lead and the contact block, thus making electrical contact. Each coil that contacts both the lead and the contact block forms a separate, redundant electrical contact. However, such common electrical connectors can be difficult to manufacture with smaller sizes, particularly as sizes of IPGs and lead pitches generally decrease. For instance, utilization of canted coiled springs in electrical connectors typically is unable to be extended to leads with millimeter or below pitches. Moreover, additional parts or functionality is commonly difficult at best to add to an electrical connector assembly having canted coiled springs. Further, contact forces associated with insertion of a lead into a conventional electrical connector assembly having canted coiled springs are not easily tuned; accordingly, difficulty of use can result since a lead commonly can buckle when attempting to insert the lead into a conventional electrical connector with a number of canted coiled springs since such springs can present a large cumulative resistance to insertion of the lead.

SUMMARY

In accordance with one or more embodiments and corresponding disclosure thereof, various aspects are described related to a connector that includes a plurality of layers patterned in two dimensions and joined in a stack with a bore there through. At least a subset of the plurality of layers are contact layers that include deflectable members (e.g., springs) that deflect in plane or out of plane upon insertion of a lead into the bore through the connector. The deflectable members form redundant electrical connections with the lead when the lead is inserted into the bore. For example, the connector can be incorporated into an implantable medical device (e.g., IPG). Moreover, methods of manufacturing a connector are set forth herein.

According to related aspects, an electrical connector is described herein. The electrical connector can include a plurality of layers with respective apertures there through, wherein the plurality of layers are joined in a stack with the respective apertures aligned to define a bore through the stack, wherein a lead is receivable in the bore. Moreover, the electrical connector can include at least one of the plurality of layers being a contact layer that includes a plurality of deflectable members, wherein the deflectable members are deflected by the lead and form electrical connections with the lead when the lead is received in the bore.

Another aspect relates to a medical system. The medical system can include a lead with a proximal end and a distal end, wherein the proximal end includes a plurality of inline contact portions separated by insulator portions, and the distal end at least one of includes or is coupled to a plurality of electrodes. Moreover, the medical system can include an implantable medical device. The implantable medical device can include a housing that is hermetically sealed to provide an enclosure for at least one of control circuitry, a power supply, or a charging coil. Further, the implantable medical device can include a header that includes a connector comprised of a plurality of contact blocks that are electrically connected to the at least one of the control circuitry, the power supply, or the charging coil, wherein the connector defines a bore through the contact blocks in which the lead is receivable to form electrical connections between the contact portions of the lead and the contact blocks, the contact blocks each include a plurality of stacked and joined layers with respective apertures there through to define the bore, and at least one of the plurality of the stacked and joined layers of each of the contact blocks being a contact layer that includes deflectable members that are deflected by the lead and form electrical connections with the contact portions of the lead when the lead is received in the bore.

Yet another aspect relates to a method of manufacturing. The method can include fabricating a plurality of layers of a connector, wherein the plurality of layers include respective apertures there through and at least a subset of the plurality of layers are contact layers that include deflectable members patterned in two dimensions. Moreover, the method can include stacking the plurality of layers with the respective apertures aligned to define a bore through a stack of the plurality of layers. Further, the method can include joining the stack of the plurality of layers to yield at least a portion of the connector with the bore there through.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE DRAWINGS

The claimed subject matter may take physical form in certain parts and arrangement of parts, embodiments of which will be described in detail in this specification and illustrated in the accompanying drawings which form a part hereof and wherein:

FIG. 3 illustrates an isometric view of connectors and lead frames from FIG. 2;

FIG. 4 illustrates an exploded view of the connectors from FIGS. 2 and 3;

DETAILED DESCRIPTION

Figure 1:
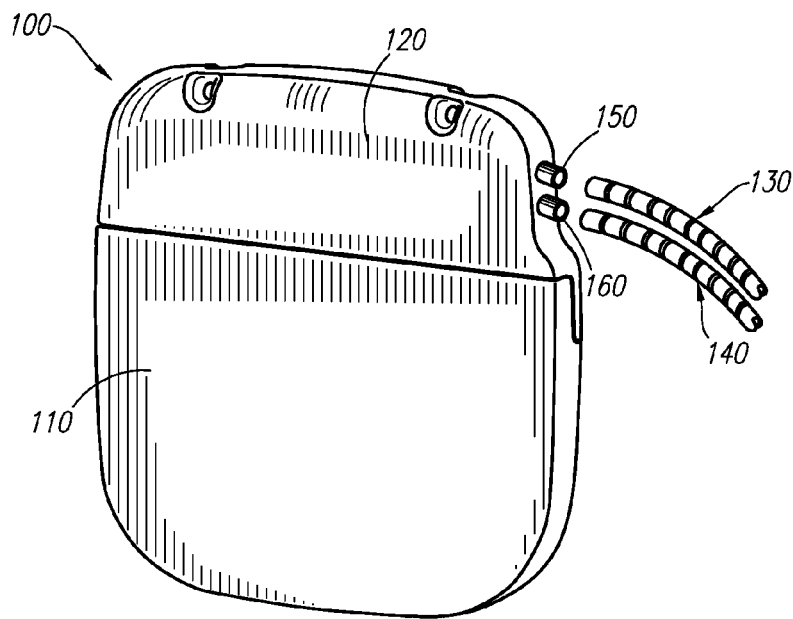
FIG. 1 illustrates an example implantable medical device comprising a housing that supports a header.

Various aspects of the claimed subject matter are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Referring now to the drawings, FIG. 1 illustrates an implantable medical device 100 comprising a housing 110 that supports a header 120. Leads 130 and 140 can be connected to the implantable medical device 100 via the header 120. Leads 130 and 140 are conductors that can be physically and electrically connected to connectors (not shown) in the header 120. For instance, proximal ends of leads 130 and 140 can respectively be inserted into connectors (not shown) that define bores 150 and 160 included in the header 120. The proximal ends of the leads 130 and 140 include a plurality of inline contacts separated by insulating portions. Further, the proximal ends of the leads 130 and 140 can have a cylindrical shape. Moreover, distal ends (not shown) of leads 130 and 140 can each include and/or can be coupled to one or more electrodes.

Each lead 130 and 140 can include substantially any number of inline contacts (e.g., contact portions) separated by insulating portions. According to an example, each lead 130 and 140 can include eight, twelve, or substantially any other number of contact portions separated by insulating portions. Moreover, each lead 130 and 140 can have substantially any diameter. By way of example, the diameter of the lead 130 or the lead 140 can be 0.050 inches; however, the claimed subject matter is not so limited. Further, the connectors in the header 120 described herein can support physically and electrically coupling with leads 130 and 140 that have smaller pitches as compared to pitches of leads with which conventional connectors can couple. For example, the leads 130 and 140 can each have a pitch that is less than 0.10 inches (e.g., the pitch can be in a range from 0.02 inches to 0.06 inches, the pitch can be in a range from 0.03 inches to 0.05 inches, the pitch can be approximately 0.04 inches, the pitch can be less than 0.04 inches, etc.).

The housing 110 is of a conductive material such as, for instance, titanium or stainless steel. Further, the housing 110 is hermetically sealed to provide an enclosure for control circuitry (not shown) connected to a power supply (not shown). The power supply, for example, can be a battery. Moreover, a charging coil (not shown) can be included in the housing 110. It is to be appreciated that the claimed subject matter is not limited to the depicted design of the housing 110; as such, any other design of the housing 110 (e.g., prismatic, cylindrical, clamshell, etc.) is intended to fall within the scope of the hereto appended claims.

The header 120 is mounted on the housing 110. The header 120 can be of molded elastomeric material, molded plastic, molded urethane, or the like. Moreover, the header 120 can comprise one or more connectors. In the illustrated example, the header 120 includes two connectors (not shown), which respectively correspond to the bores 150 and 160; yet, it is contemplated that the claimed subject matter is not so limited and instead can include one connector or more than two connectors.

The proximal ends of leads 130 and 140 can be plugged into the connectors comprised in the header 120 via the bores 150 and 160. When plugged in (e.g., physically connected), the leads 130 and 140 are electrically connected to the control circuitry and power supply contained in the housing 110. Further, the distal ends of the leads 130 and 140 can connect to respective electrodes. Additionally or alternatively, the distal ends of the leads 130 and 140 can include respective electrodes.

The electrodes can be surgically secured to body tissue whose proper functioning is assisted by the implantable medical device 100. The implantable medical device 100 that includes one or more connectors as described herein can be any one of a number of known implantable therapeutic devices such as a SCS device, a vagus nerve stimulation device for treating epilepsy, an electrical stimulation device for treating paralysis, and so forth. According to other examples, the implantable medical device 100 that includes one or more connectors as described herein can be a cardiac pacemaker, an implantable cardiac defibrillator (ICD), an implantable neurological stimulator, a general implantable stimulator, an implantable monitor such as a loop recorder, or the like. For example, if the implantable medical device 100 that includes one or more connectors as set forth herein is an IPG for spinal cord stimulation to control pain, the circuitry comprised in the housing 110 provides a pulsed stimulating signal that can be current controlled or voltage controlled. The stimulating signal is delivered to nerves entering the spinal cord via the leads 130 and 140, which terminate at the electrodes.

The implantable medical device 100 (e.g., IPG, etc.) can be surgically placed inside the body along with the leads 130 and 140, with electrodes surgically secured to body tissue as discussed above. One end of each of the leads 130 and 140 is electrically and physically connected to the implantable medical device 100 via the header 120, while the other end of each of the leads 130 and 140 is placed in or near the tissue to be electrically stimulated (e.g., the spinal column). The second end of each of the leads 130 and 140 includes or is connected to exposed electrodes. Thus, the exposed electrodes are electrically connected to the implantable medical device 100, and can transfer electrical stimulation pulses generated by the implantable medical device 100 to the tissue.

As set forth in greater detail below, connectors described herein are made up of a stack of thin layers that have been patterned in two dimensions. The connectors, for instance, can be used inside the header 120 of an IPG; yet, it is further contemplated that the connectors described herein can be used in any application where a short contact is desired. The design of the connectors allows for many independent contact structures with a specifically designed contact force. Accordingly, the connectors set forth herein can be less costly to manufacture, shorter than, smaller than, etc. conventional connectors, while enabling reliable formation of physical and electrical connections with leads inserted therein.

At least a subset of the layers of a connector provided herein are contact layers that include a plurality of deflectable members. The deflectable members can be cantilevered beams, cantilevered serpentine structures, cantilevered spirals, simply supported beams, or other features that deflect either in or out of plane to make contact with a lead (e.g., the lead 130, the lead 140, etc.), which can be a cylindrical pin or surface, that is inserted through a contact layer that includes the deflectable members. For instance, cantilevered structures can be deformable in a plane and structures in torsion (e.g., simply supported beams, etc.) can be deformable out of a plane; yet, the claimed subject matter is not so limited. Moreover, one or more additional types of layers can be included in the connector; the additional types of layers can provide stops to limit motion (e.g., stop layers), allow space for contact layer features to move (e.g., spacer layers), and limit lead insertion position (e.g., outer layers).

Deflectable members of contact layers are individually fabricated, and thus, mechanical behavior of each deflectable member can be adjusted as desired to interact with an inserted lead. Accordingly, an insertion force needed for inserting a lead into a connector comprised of a stack of layers, including the contact layers with the deflectable members, can be tunable based upon the mechanical properties of the deflectable members as patterned. For example, a lower insertion force can be yielded for a connector that has a larger number of inline contacts; in contrast, conventional connectors with a larger number of inline contacts oftentimes are difficult to use since a lead can buckle when attempting to insert the lead therein due to higher insertion force for the conventional connectors.

Layers of a connector described herein can be held together in various manners. For example, layers can be joined mechanically through use of fasteners, through mechanical upsetting, bending or folding, by employing adhesives, or through pressure, welding (e.g., resistance welding, etc.), or diffusion bonding. Accordingly, at least a subset of the layers of a connector can be stacked with respective apertures there through aligned (e.g., centers of the respective apertures can be aligned to define a bore through a stack of the layers), and the layers can be joined together via one or more of the foregoing approaches.

Moreover, layers can be fabricated using any technique that can pattern thin layers with small features. Example fabrication techniques include wire electric discharge machining (EDM), laser cutting, or photolithography. For instance, photolithographic approaches can be used to efficiently create complicated two dimensional patterns for the layers. Some example photolithographic approaches include metal photoetching, electroforming, or thin film/microelectronics techniques.

As each layer can be made in a sheet, the sheets can be alignable so that multiple sheets can be aligned and individual contact layers, and accordingly individual deflectable members, can be created in a batch fashion. A further refinement can be to also create insulating and sealing elements described herein, which are part of the connector stack, into sheets that can be assembled along with the contact layers.

The two dimensional patterning can enable long segments or features to more easily be incorporated into connectors, or contact blocks included therein, than is practical in a conventional machined contact block. For instance, these long segments or features can be for attachment, packaging, wire routing, or the like. Moreover, such long segments or features can be bent or folded using a sheet metal technique.

The connectors described herein can support repeated cycles of insertion and removal of leads without permanent deformation of the deflectable members or loss of function. Further, a contact resistance can be approximately 0.8 Ohm; yet, the claimed subject matter is not so limited.

Figure 2:
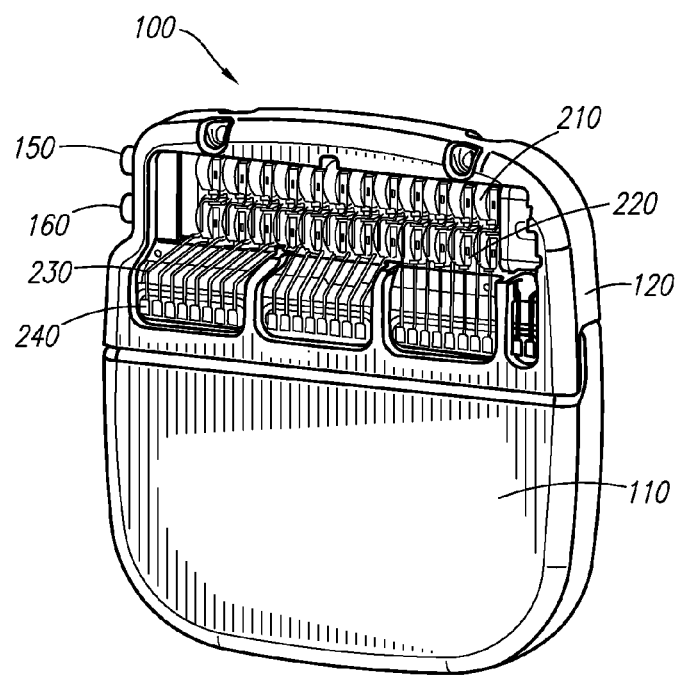
FIG. 2 illustrates another example of the implantable medical device with a portion of a side wall of the header removed to provide a view of components enclosed there within.

Now turning to FIG. 2, illustrated is another example of the implantable medical device 100 with a portion of a side wall of the header 120 removed to provide a view of components enclosed there within. Two connectors 210 and 220 are enclosed within the header 120. The connector 210 defines the bore 150, and the connector 220 defines the bore 160. The lead 130 from FIG. 1 can be receivable in the bore 150 of the connector 210, and the lead 140 from FIG. 1 can be receivable in the bore 160 of the connector 220. While two connectors 210 and 220 are depicted in FIG. 2, it is contemplated that substantially any number of connectors, each substantially similar to the connector 210 or the connector 220, can be included in the implantable medical device 100. Moreover, while the connector 210 is shown to be positioned above the connector 220 in the housing 120, any other orientation of the connectors 210 and 220 relative to each other or in relation to the housing 120 generally is intended to fall within the scope of the hereto appended claims.

The connectors 210 and 220 each include a stack of contact blocks separated by seals. Moreover, the contact blocks in the connectors 210 and 220 are coupled to respective lead frames (e.g., a lead frame 230, etc.). According to an example, a contact block can have a flat surface, and a lead frame can be welded to the flat surface of the contact block. As shown in FIG. 2, the lead frames can extend from the contact blocks and can be coupled to respective feed through (FT) pins (e.g., the lead frame 230 is coupled to a FT pin 240, etc.). The FT pins can be platinum pins that extend from the header 120 to the housing 110. Further, the FT pins can be housed in one or more ceramic blocks.

It is contemplated, however, that contact blocks having substantially any shape are intended to fall within the scope of the hereto appended claims. For example, the shape of the contact blocks is a function of a shape of a perimeter of layers of the contact block where the perimeter of the layers can be circular, square, rectangular, or have substantially any other shape. Moreover, the perimeter can include an extension, a flat portion, etc. According to an illustration, the shape of the contact blocks, and thus the shape of the connector including the contact blocks, can be made to mount within a header (e.g., the header 120 of FIG. 1) of an implantable medical device (e.g., the implantable medical device 100 of FIG. 1). Pursuant to other examples, contact blocks need not have flat surfaces to which lead frames can be welded, contact blocks can extend towards to the FT pins thereby decreasing the length of the lead frames or mitigating need for inclusion of the lead frames (e.g., extensions incorporated into the contact blocks can respectively be welded to corresponding FT pins such that lead frames need not be employed), and so forth. Further examples depicting various contact block shapes are described in greater detail below.

Turning to FIG. 3, illustrated is an isometric view of the connectors 210 and 220 and lead frames from FIG. 2. Pursuant to this example, the connector 210 includes twelve contact blocks that are stacked inline (e.g., a contact block 310, etc.). Moreover, each of the twelve contact blocks is coupled to a respective lead frame. Hence, twelve lead frames are connected to the connector 210. For instance, a first end 330 of a lead frame 320 is coupled to the contact block 310, and a second end 340 of the lead frame 320 is coupled to a FT pin (not shown). As noted above, the contact block 310 can have a flat surface, to which the first end 330 of the lead frame 320 can be welded. The other contact blocks of the connector 210 can be substantially similar to the contact block 310, and the other lead frames coupled to the other contact blocks of the connector 210 can be substantially similar to the lead frame 320. Moreover, it is to be appreciated that the connector 220 can be substantially similar to the connector 210. Further, as set forth above, it is contemplated that depending upon the shape of the contact blocks of the connectors 210 and 220, lead frames with differing shapes can be employed (e.g., lead frames can be shortened), lead frames need not be employed (e.g., the contact blocks can be welded to corresponding FT pins), and so forth.

FIG. 4 depicts an exploded view of the connectors 210 and 220 from FIGS. 2 and 3. The connector 210 includes twelve contact blocks 402-424 (e.g., the contact block 310 of FIG. 3, etc.) separated by twelve seals 426-448. Further, the connector 220 includes twelve contact blocks 450-472 separated by twelve seals 474-496. The seals 426-448 and 474-496 can be made of silicone, for instance. The seals 426-448 and 474-496 isolate neighboring contact blocks 402-424 and 450-472. Moreover, the connectors 210 and 220 include insulators (e.g., an insulator 498); the insulators can be made of plastic, for example.

As provided in FIGS. 2-4, the implantable medical device 100 can include two connectors 210 and 220, each having twelve contact blocks. However, it is contemplated that the implantable medical device 100 can comprise substantially any number of connectors, and the connectors can include substantially any number of contact blocks (e.g., the header 120 of the implantable medical device 100 can comprise three connectors that respectively include eight contact blocks, etc.). Moreover, while the connector 210 and the connector 220 are described above as being substantially similar, it is to be appreciated that differing connectors can be included in the implantable medical device 100 (e.g., the connectors can have differing numbers of contact blocks, differing configurations, differing dimensions, etc.).

The contact blocks 402-424 and 450-472 are each made up of a stack of thin layers that are patterned in two dimensions. At least one of the layers in each of the contact blocks 402-424 and 450-472 is a contact layer that includes a plurality of deflectable members (e.g., springs). The deflectable members are deflectable by a lead (e.g., deformed through physical touching by the lead) and can form electrical connections with the lead. The deflectable members can be deflected in a plane or out of a plane to make contact with the lead (e.g., a cylindrical pin, surface, etc.).

According to an example, the deflectable members can be cantilevered beams. By way of another example, the deflectable members can be cantilevered spirals. Pursuant to yet another example, the deflectable members can be cantilevered serpentine structures. In accordance with a further example, the deflectable members can be simply supported beams that comprise flags, where the simply supported beams can be twisted by the flags being displaced by the lead. However, it is contemplated that the claimed subject matter is not limited to the above-noted examples of deflectable members. Moreover, further discussion of the example deflectable members is set forth herein.

Moreover, other layers in the contact blocks 402-424 and 450-472 can include spacer layers, outer layers, and stop layers. A spacer layer provides room for the deflectable members of a contact layer to move freely. An outer layer can make contact with a lead as it is inserted in a contact block, and can limit a range of motion of the lead. Moreover, a stop layer can limit out of plane motion of the deflectable members of a contact layer. A contact block from the contact blocks 402-424 and 450-472 can include at least one spacer layer, at least one outer layer, and at least stop layer in addition to at least one contact layer. However, it is to be appreciated that such contact block need not include all three types of layers (e.g., spacer, outer, and stop layers) in addition to the at least one contact layer, and instead can include a subset or none of these three types of layers (e.g., zero, one or two types of layers out of spacer layers, outer layers, and stop layers) along with the at least one contact layer.

Figure 5:
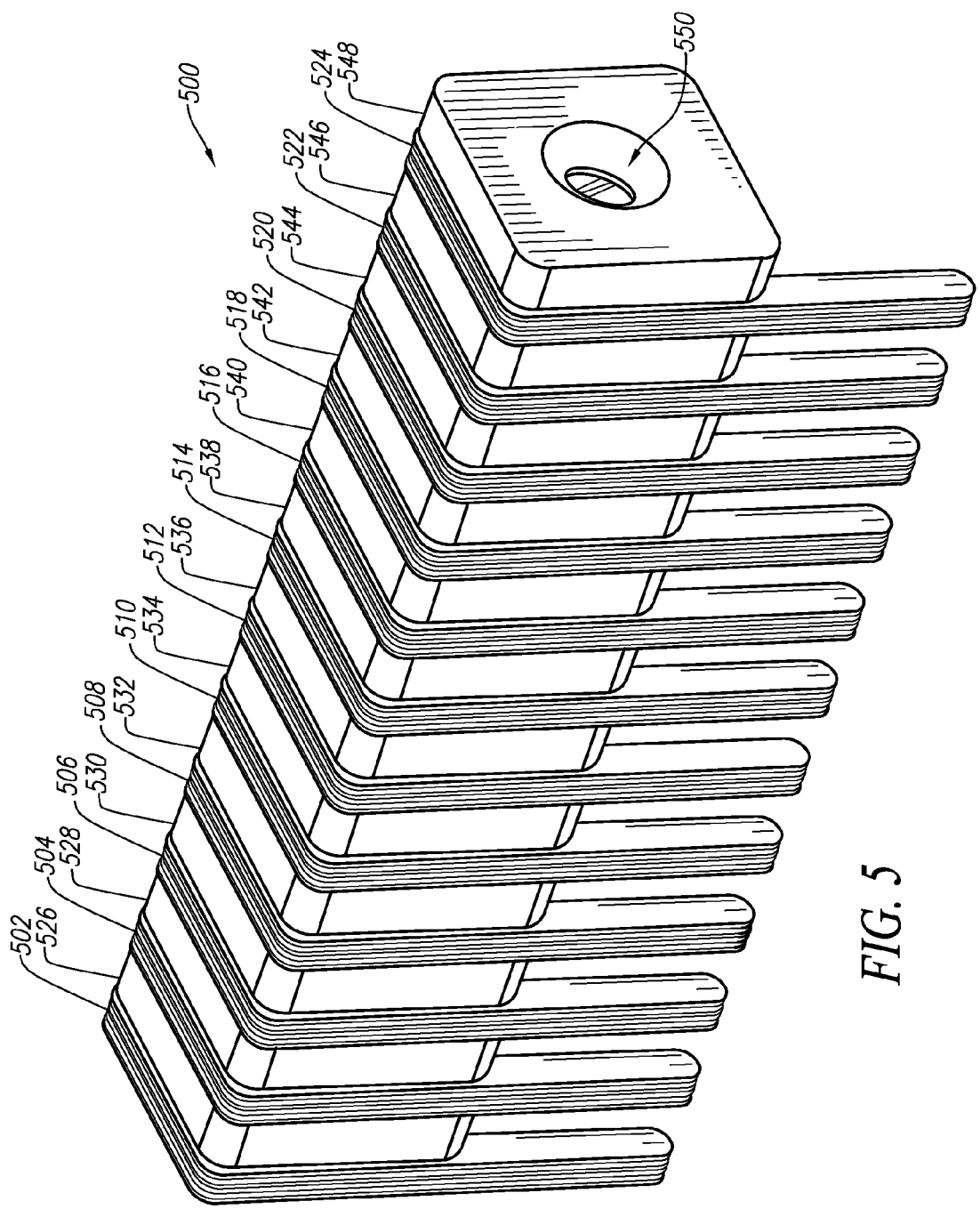
FIG. 5 illustrates another example connector that can be included in a header of an implantable medical device.

With reference to FIG. 5, illustrated is another example connector 500 that can be included in a header (e.g., the header 120 of FIG. 1) of an implantable medical device (e.g., the implantable medical device 100 of FIG. 1). The connector 500 includes twelve contact blocks 502-524, which are each made up of a stack of thin layers that are patterned in two dimensions; yet, it is contemplated that more or less than twelve contact blocks 502-524 can be included in the connector 500. Moreover, at least one layer in each of the twelve contact blocks 502-524 is a contact layer. Further, the twelve contact blocks 502-524 are separated by twelve seals 526-548. The seals 526-548 can be made of silicone, for instance. Similar to the seals 426-448 and 474-496 from FIG. 4, the seals 526-548 isolate neighboring contact blocks 502-524 (e.g., the seal 526 isolates the contact block 502 from the contact block 504, etc.).

The connector 500 can define a bore 550 through the contact blocks 502-524 and seals 526-548. A lead (e.g., the lead 130, the lead 140, etc.) (not shown) can be receivable in the bore 550. For instance, a lead can deflect deflectable members of contact layers of the contact blocks 502-524 as the lead is inserted into the bore 550, and the deflectable members can remain deflected while the lead remains positioned in the bore 550. The deflectable members can supply forces that cause the lead to remain inserted in the bore 550. Moreover, when inserted in the bore 550, electrical connections can be formed between contact portions of the lead and the deflectable members of the contact layers of the contact blocks 502-524. When the lead is removed from the bore 550, the deflectable members can return to respective undeflected states.

According to an example, a length of the connector 500 from an outer surface of the contact block 502 to an outer surface of the seal 548 is less than 1 inch. Following this example, the contact blocks 502-524 can each respectively be 0.040 inches and the seals 526-548 can each respectively be 0.040 inches. Thus, a lead with a 0.040 pitch can be coupled with the connector 500. However, it is to be appreciated that the claimed subject matter is not limited to the foregoing example.

Figure 6:
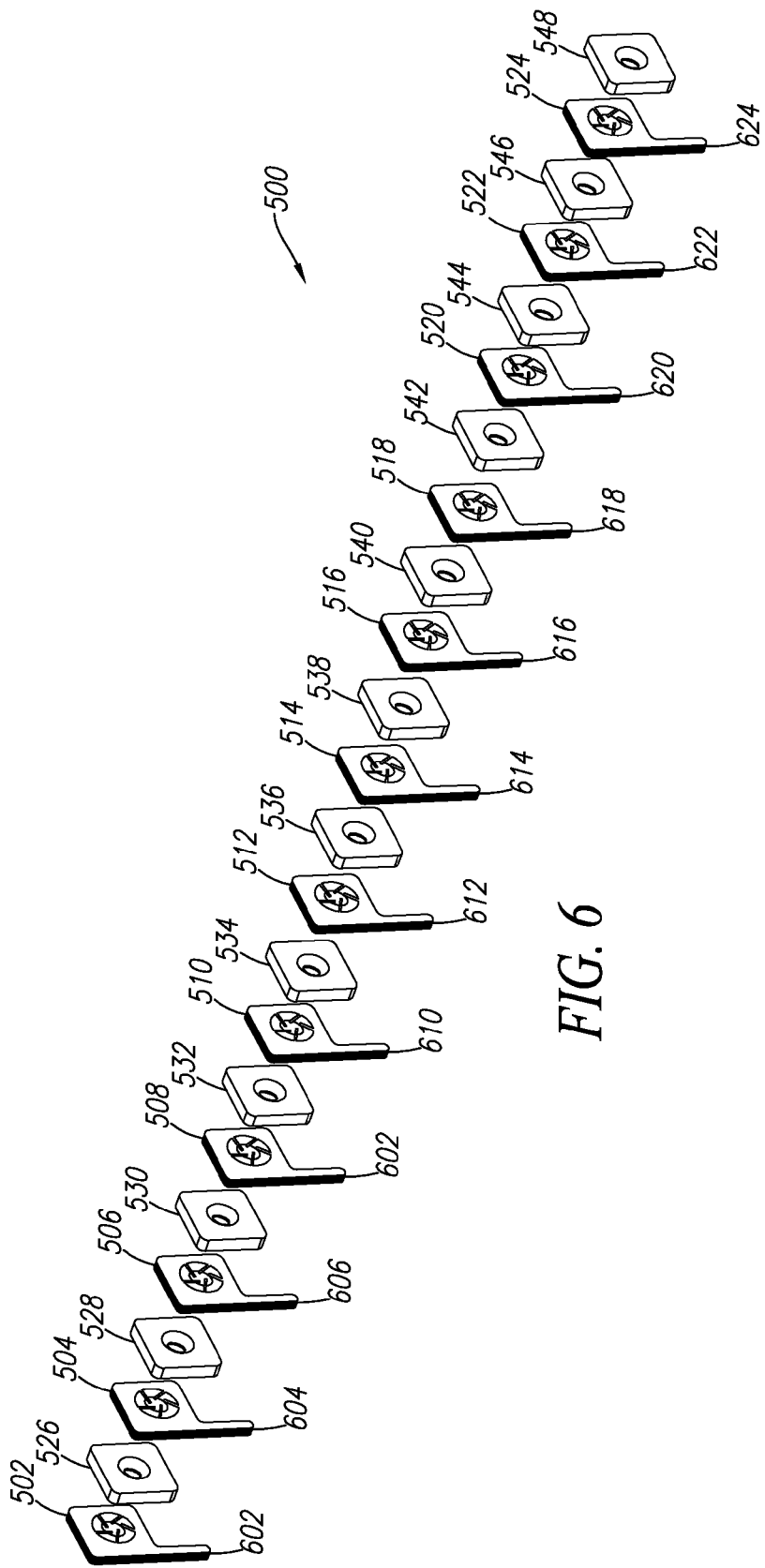
FIG. 6 illustrates an exploded view of the connector from FIG. 5.

Turning to FIG. 6, illustrated is an exploded view of the connector 500 from FIG. 5. As depicted, apertures through the contact blocks 502-524 and the seals 526-548 can be aligned in the connector 500 to define a bore (e.g., the bore 550) through the connector 500, where a lead is receivable in the bore.

The contact blocks 502-524 each include a respective extension 602-624 built into the corresponding contact block 502-524 (e.g., the contact block 502 includes the extension 602, etc.). The extensions 602-624 can be welded to respective FT pins (not shown), which pass through from a header (e.g., the header 120 of FIG. 1) to a housing (the housing 110 of FIG. 1) of an implantable medical device (e.g., the implantable medical device 100 of FIG. 1). Thus, the extensions 602-624 can shorten FT pins (e.g., which are commonly expensive). Additionally or alternatively, the extensions 602-624 can mitigate use of or shorten lead frames between the contact blocks 502-524 and the FT pins. Accordingly, by shortening FT pins (e.g., which can reduce the amount of platinum used), eliminating lead frames, and/or shortening lead frames, manufacturing costs for the implantable medical device with the connector 500 can be lower as compared to a device that incorporates a conventional connector.

Figure 7:
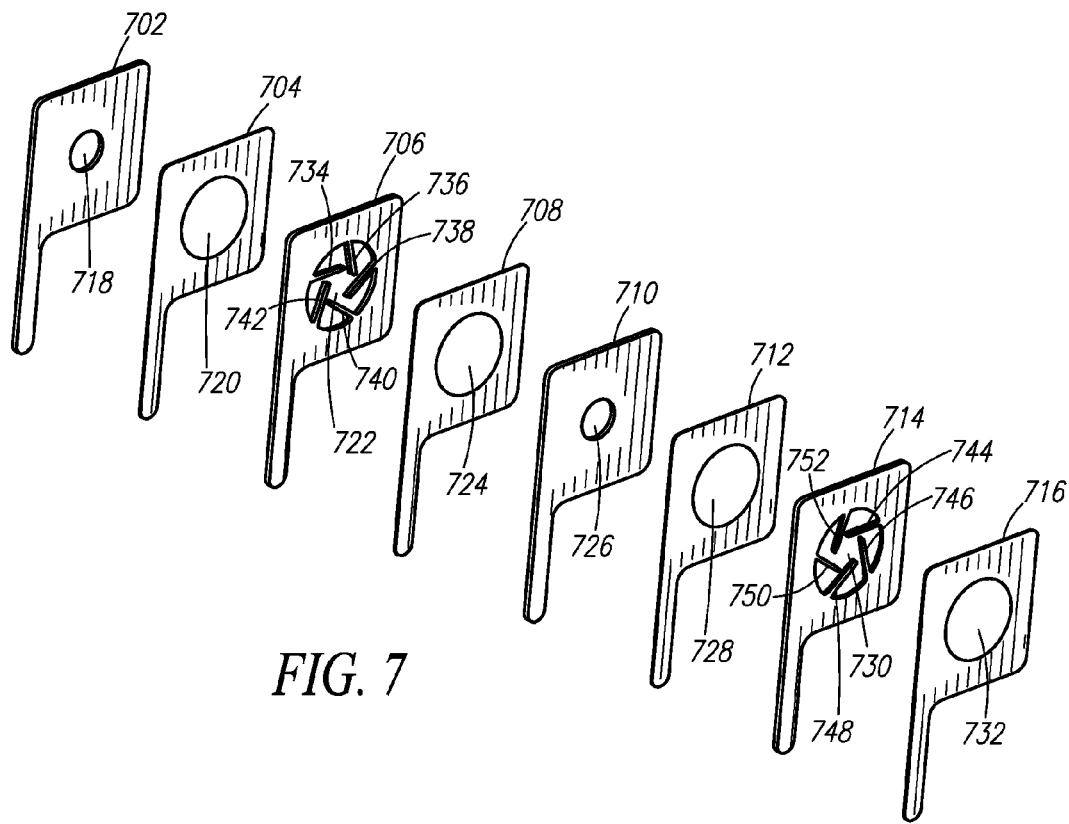
FIG. 7 illustrates an exploded view of a contact block from a connector.

Referring now to FIG. 7, illustrated is an exploded view of a contact block 700. For example, the contact block 700 can be one of the contact blocks 502-524 of the connector 500 from FIGS. 5 and 6; however, the claimed subject matter is not so limited. The contact block 700 includes a plurality of layers 702-716. While the contact block 700 is depicted as including eight layers 702-716, it is to be appreciated that a contact block with more or less than eight layers is intended to fall within the scope of the hereto appended claims.

The layers 702-716 are thin layers that have been patterned in two dimensions. Moreover, the layers 702-716 each have a respective aperture 718-732 there through. When the layers 702-716 of the contact block 700 are joined in a stack, the respective apertures 718-732 are aligned to define a bore through the stack. Further, a lead can be receivable in the bore through the apertures 718-732 of the layers 702-716 (as well as through apertures (not shown) of layers (not shown) of other contact blocks (not shown) and/or through bores (not shown) through seals (not shown) in a connector).

The layer 702 is an outer layer that can make contact with a lead as it is inserted into the bore defined through the apertures 718-732. For instance, the lead can be inserted from a side of the contract block 700 where the outer layer 702 is positioned and can pass in a direction from the outer layer 702 to the layer 716. The outer layer 702 can limit a range of motion of the lead. Moreover, the outer layer 702 can align the lead for insertion through the bore. According to an example, the outer layer 702 can be thicker than other layers 704-716 of the contact block 700. Following this example, the outer layer 702 can be thicker when the outer layer 702 aligns the lead to pass through a center of the bore, thereby providing support to withstand a force associated with the lead pushing into an outer surface of the outer layer 702 when attempting to insert the lead. By way of example, the outer layer 702 can be approximately 0.007 inches thick; yet, it is to be appreciated that other thicknesses of the outer layer 702 are intended to fall within the scope of the hereto appended claims. Moreover, it is contemplated that the outer layer 702 need not be thicker than the other layers 704-716 of the contact block 700; for instance, if another alignment system is used to cause the lead to pass through the center of the bore, then the outer layer 702 can have a thickness that is substantially similar to thicknesses of one or more of the other layers 704-716.

The layer 704 is a spacer layer that supplies room for deflectable members of an adjacent contact layer (e.g., the layer 706) to move freely. The aperture 720 of the spacer layer 704 has a larger diameter compared to the aperture 718 of the outer layer 702. According to an example, the spacer layer 704 can be approximately 0.001 inches thick; however, it is to be appreciated that the claimed subject matter is not so limited.

The layer 706 is a contact layer that includes a plurality of deflectable members 734-742. As depicted in the example illustrated in FIG. 7, the deflectable members 734-742 are cantilevered beams. The contact layer 706 comprises five deflectable members 734-742 (e.g., cantilevered beams); however, it is contemplated that a contact layer with substantially any number of deflectable members is intended to fall within the scope of the hereto appended claims.

The deflectable members 734-742 extend into the aperture 722 through the contact layer 706. The deflectable members 734-742 can be deflected by the lead inserted through the aperture 722; thus, the deflectable members 732-742 and the lead inserted through the aperture 722 are physically connected. Moreover, when the lead is inserted through the aperture 722, the deflectable members 734-742 can form electrical connections with the lead. Since the contact layer 706 includes the plurality of deflectable members 734-742 (e.g., five in the depicted example), a plurality of redundant electrical connections (e.g., five in the depicted example) can be formed between a contact portion of the lead and the contact layer 706. Further, once the lead is positioned through the aperture 722, the deflectable members 734-742 supply forces upon the lead causing the lead to be physically retained in such position.

According to an example, the contact layer 706 can have a thickness within a range from 0.002 inches to 0.006 inches. By way of another example, the contact layer 706 can have a thickness within a range from 0.003 inches to 0.005 inches. Pursuant to yet further examples, the contact layer can have a thickness of approximately 0.0030 inches, approximately 0.0035 inches, approximately 0.0040 inches, approximately 0.0050 inches, approximately 0.0060 inches, or the like. Yet, the claimed subject matter is not limited by the foregoing examples. In accordance with yet another example, the thickness of the contact layer 706 (as well as other layers of the contact block 700) can increase or decrease as a function of a diameter of the lead that is receivable in a bore of the contact block 700 (e.g., thicknesses of the layers can be sub 0.001 inches with a small lead or wire connector, etc.).

Moreover, an inner diameter of the undeflected deflectable members 734-742 (e.g., through a center portion of the aperture 722) can be approximately 0.040 inches, approximately 0.045 inches, or substantially any other inner diameter, for example. Following the foregoing example, if a lead with an outer diameter of 0.050 inches is inserted through the aperture 722, the deflectable members 734-742 can be deformed outwards (e.g., deflect approximately 0.005 inches, approximately 0.010 inches, etc.) to allow the lead to pass thereby. For instance, when patterning a contact layer, the number of deflectable members that can be included in contact layer is limited be a desired deflection of the deflectable members.

The layer 708 is a spacer layer. The spacer layer 708 can be substantially similar to the spacer layer 704. Pursuant to an example, a contact layer in a contact block of a connector can have spacer layers adjacently located on both sides thereof within the stack (e.g., the spacer layer 704 and the spacer layer 708 are adjacently located on each side of the contact layer 706). By having the spacer layer 704 and the spacer layer 708 positioned adjacent to the contact layer 706, the deflectable members 734-742 can freely move within the space defined by the aperture 720 and the aperture 724. Thus, the spacer layer 704 and the spacer layer 708 are thin shims that allow for the deflectable members 734-742 to move (e.g., slightly out of plane) in response to a force applied by the lead without physically contacting another portion of the contact block 700.

The layer 710 is a stop layer that limits side to side motion of deflectable members of contact layers in the contact block 700. The side to side motion of deflectable members is limited to a thickness of a spacer layer by the stop layer 710. For instance, motion of the deflectable members 734-742 in a direction towards the stop layer 710 is limited to a thickness of the spacer layer 708. Accordingly, the stop layer 710 limits out of plane deflection of the deflectable members, and instead helps guide the deflectable members to deflect in the plane. The aperture 726 of the stop layer 710 has a smaller diameter as compared to the aperture 724 of the spacer layer 708. Further, the diameter of the aperture 726 of the stop layer 710 can be substantially similar to the diameter of the aperture 718 of the outer layer 702; however, the claimed subject matter is not so limited.

Moreover, the layer 712 is a spacer layer, the layer 714 is a contact layer, and the layer 716 is a spacer layer. The spacer layer 712 and the spacer layer 716 are substantially similar to the spacer layer 704 and the spacer layer 708.

The contact layer 714 can be substantially similar to the contact layer 706 with a plurality of deflectable members 744-752 that are opposite facing as compared to the deflectable members 734-742 of the contact layer 706. Again, five deflectable members 744-752 (e.g., cantilevered beams) are shown as being included in the contact layer 714, yet, the claimed subject matter also contemplates more or less than five deflectable members being included in a contact layer.

Each layer 702-716 can be made of identical conductive material that can be formed and joined together to yield a single piece, namely, the contact block 700. Examples of the conductive material from which the layers 702-716 can be formed include titanium or stainless steel (e.g., grade 304). Other examples of suitable materials for the layers 702-716 include carbon such as pyrolytic carbon, zirconium, niobium, molybdenum, palladium, hafnium, tantalum, tungsten, iridium, platinum, gold, nickel, chromium, or alloys thereof (e.g., nickel alloy MP35N, etc.). By way of another example, the contact layers 706 and 714 can be made of identical conductive material, while one or more of the other layers (e.g., one or more of the outer layer 702, the spacer layer 704, the spacer layer 708, the stop layer 710, the spacer layer 712, or the spacer layer 716) can be made of a differing material. The differing material can be a non-conductive material (e.g., the differing material can be a plastic). For instance, the one or more of the other layers can be made of the differing material since such layer(s) need not be part of the electrically conductive path (e.g., electrically coupled to the lead).

When the lead is inserted through the respective apertures 718-732 that define the bore, the deflectable members 734-742 of the contact layer 706 and the deflectable members 744-752 of the contact layer 714 deform outwardly in a plane towards perimeters of the apertures 722 and 730, respectively. In the example shown in FIG. 7, when the layers 702-716 are assembled, the contact block 700 can form ten individual, redundant electrical connections with the inserted lead. As thicknesses of the layers 702-716 are decreased, an advantage of a connector that includes the contact block 700 is that multiple electrical contacts can be made to a lead within a very short distance (e.g., a thickness of the contact block 700 can be 0.040 inches or less).

Figure 8:
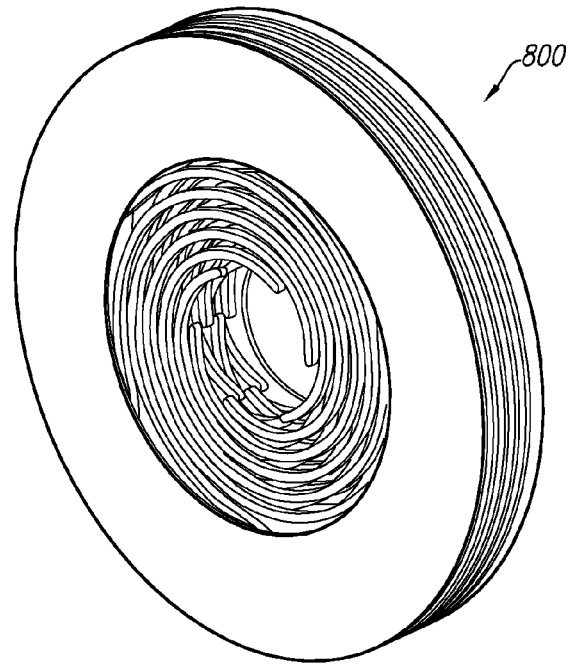
FIG. 8 illustrates another example contact block.

Now referring to FIG. 8, illustrated is another example contact block 800. The contact block 800 includes a plurality of contact layers, each of which include a plurality of deflectable members that are cantilevered spirals. For example, four contact layers can be included in the contact block 800, and each of the four contact layers can include six individual cantilevered spirals. Following this example, the contact block 800 can form twenty-four individual contacts with a contact portion of a lead inserted through the bore of the contact block 800. Yet, it is to be appreciated that the claimed subject matter is not limited to the foregoing example, as any number of contact layers and/or any number of cantilevered spirals integrated into each of the contact layers can be leveraged.

Moreover, a spacer layer is in between each of the contact layers in the contact block 800 to allow for each cantilevered spiral in the contact layers to move freely. In the example depicted in FIG. 8, an outer layer, which can be similar to the outer layer 702 of FIG. 7, is removed from a front of the contact block 800. Moreover, it is contemplated that the contact block 800 can include one or more stop layers in the stack; however, the claimed subject matter is not so limited.

With reference to FIGS. 9-12, illustrated are various example two dimensional patterns that can be employed for a contact layer included in a connector as described herein. It is to be appreciated, however, that the two dimensional patterns are provided for illustration purposes, and other two dimensional patterns for a contact layer are intended to fall within the scope of the hereto appended claims. For instance, it is to be appreciated that a number of deflectable members can vary from the examples shown in FIGS. 9-12 (e.g., more deflectable members or fewer deflectable members can be included in a contact layer). Moreover, shapes of deflectable members in addition to the examples depicted in FIGS. 9-12 are intended to fall within the scope of the claims appended hereto. Further, while the examples from FIGS. 9-12 each show a circular outside perimeter for the contact layer, it is to be appreciated that outside perimeters of the contact layers can be substantially any shape. For instance, by way of example and not limitation, the outside perimeters of the contact layers can be substantially similar to the outside perimeters of the layers 702-716 from FIG. 7.

By way of example, a contact layer (e.g., from FIGS. 9-12) includes deflectable members that have respective portions that are formed integral with a remainder of the contact layer. Thus, the deflectable members and the remainder of the contact layer are contiguous. Accordingly, an electrical connection between the deflectable members and the remainder of the contact layer, and hence a contact block in which the contact layer is included upon stacking and joining, is permanently formed. In contrast, conventional connectors that include coiled springs with welded ends positioned within grooves of contact blocks need to form electrical connections between both a lead and the spring and between the spring and the contact block upon insertion of a lead. Hence, the connectors described herein remove a failure point (e.g., forming of the electrical connection between the deflectable member and the contact block is no longer a failure point).

Figures 9, 10:
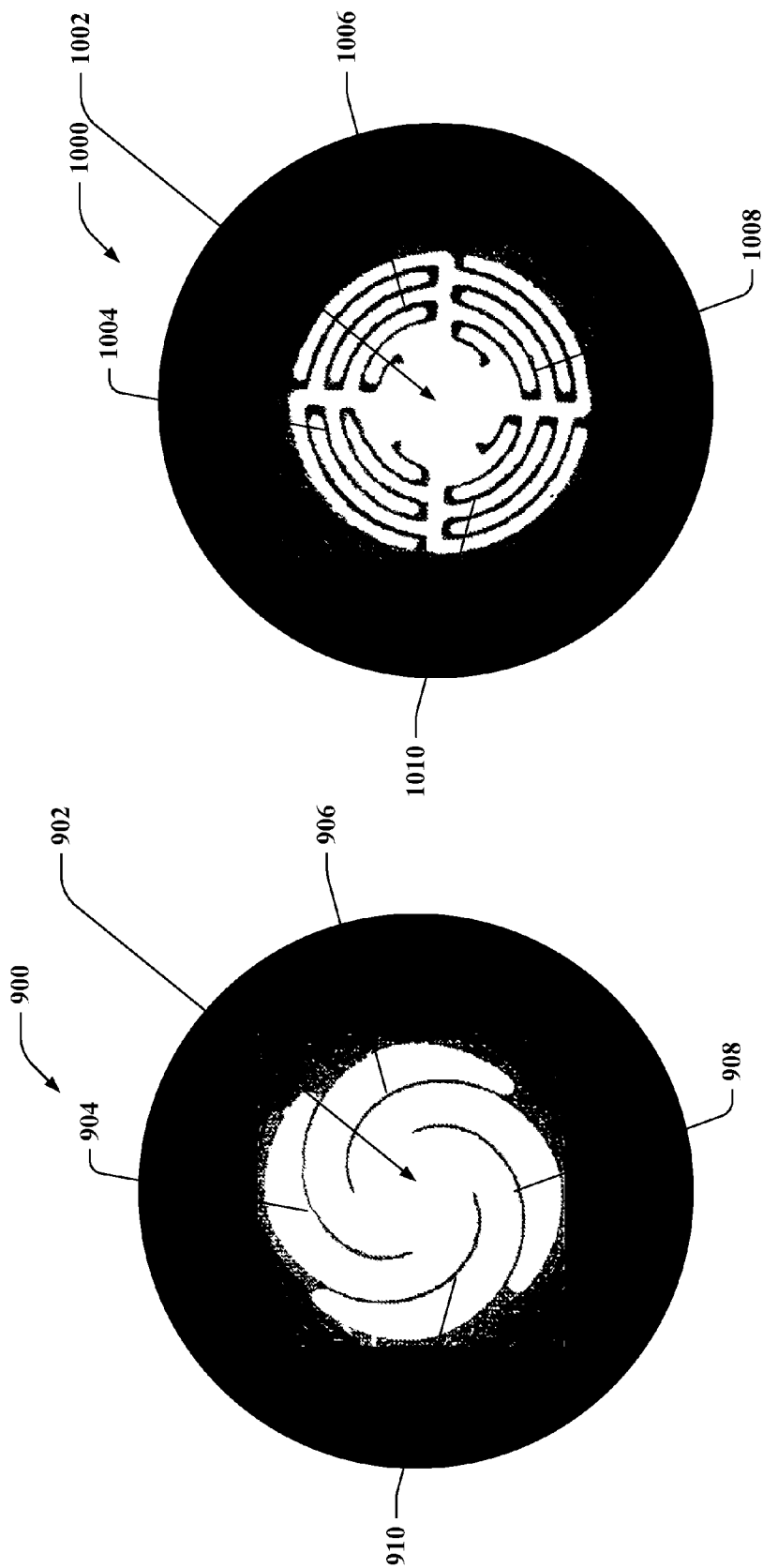
FIGS. 9-12 illustrate various example two dimensional patterns that can be employed for a contact layer included in a connector as described herein.

Turning to FIG. 9, illustrated is an example contact layer 900 that has an aperture 902 there through. The deflectable members included in the contact layer 900 are cantilevered spirals 904-910. According to an example, the cantilevered spirals 904-910 can be tapered or untapered. A lead inserted through the aperture 902 physically contacts ends of the cantilevered spirals 904-910 located closest to a center of the aperture 902, which causes the cantilevered spirals 904-910 to deflect outward from the center of the aperture 902 in a plane. Electrical connections are formed between a contact portion of the lead and the deflected cantilevered spirals 904-910 when the lead is inserted through the aperture 902. Moreover, when the lead is removed from the aperture 902, the cantilevered spirals 904-910 return to the undeflected state as shown.

With reference to FIG. 10, illustrated is another example contact layer 1000 that has an aperture 1002 there through. The deflectable members included in the contact layer 1000 are cantilevered serpentine structures 1004-1010. When a lead is inserted through the aperture 1002, the lead physically contacts ends of the cantilevered serpentine structures 1004-1010 located closest to a center of the aperture 1002. Accordingly, the cantilevered serpentine structures 1004-1010 are deflected outward from the center of the aperture 1002 in a plane, and electrical connections are formed between a contact portion of the lead and the deflected cantilevered serpentine structures 1004-1010 when the lead is inserted through the aperture 1002. Further, when the lead is removed from the aperture 1002, the cantilevered serpentine structures 1004-1010 return to the undeflected state as depicted.

Figures 11, 12:
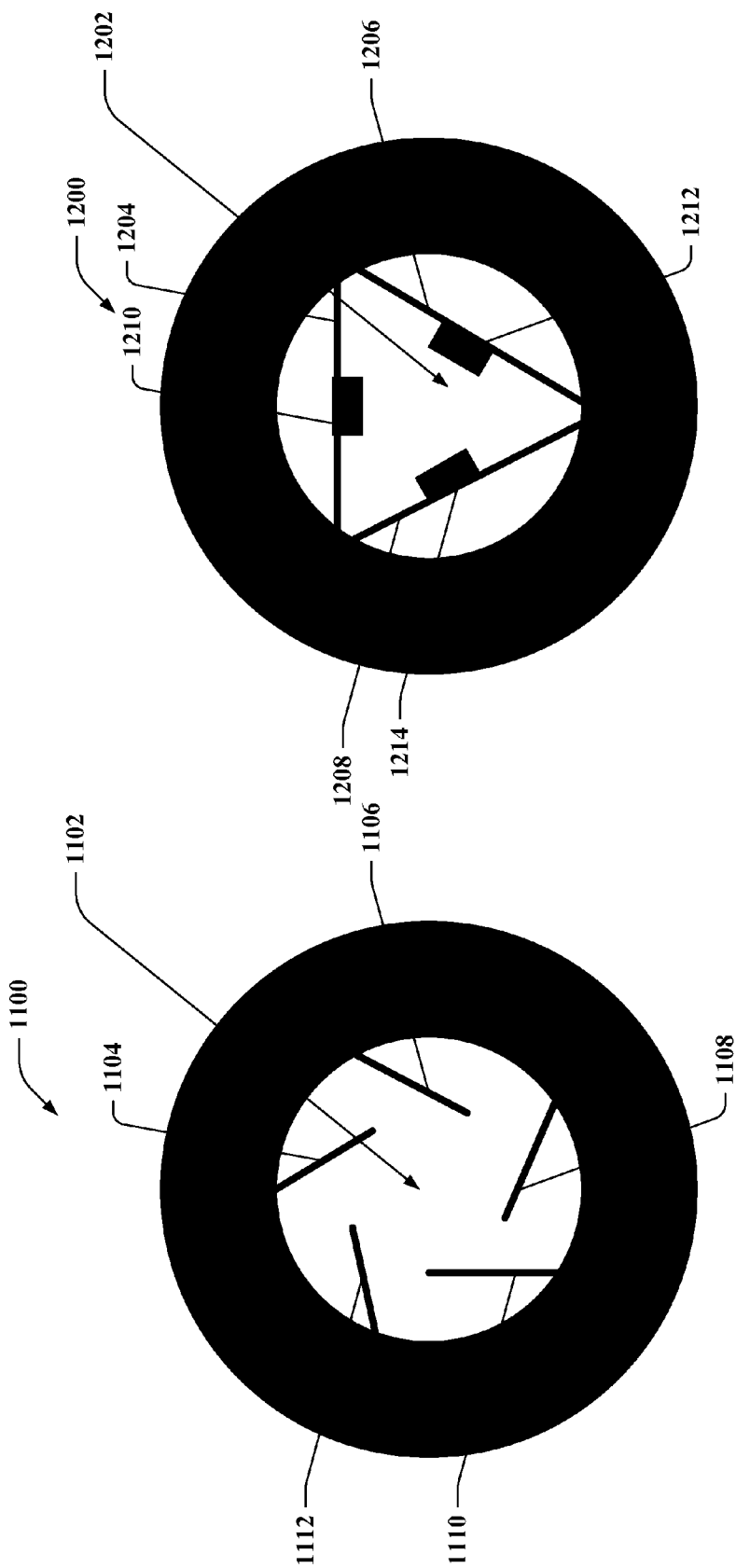

Turning to FIG. 11, illustrated is yet a further example contact layer 1100 that has an aperture 1102 there through. The deflectable members included in the contact layer 1100 are cantilevered beams 1104-1112, which can be substantially similar to the example of FIG. 7. When a lead is inserted through the aperture 1102, the lead physically contacts ends of the cantilevered beams 1104-1112 located closest to a center of the aperture 1102. Thus, the cantilevered beams 1104-1112 are deflected outward from the center of the aperture 1102 in a plane upon the lead being inserted through the aperture 1102. Moreover, electrical connections are formed between a contact portion of the lead and the deflected cantilevered beams 1104-1112 when the lead is inserted through the aperture 1102. Upon the lead being removed from the aperture 1102, the cantilevered beams 1104-1112 return to the undeflected state shown in FIG. 11.

Referring next to FIG. 12, illustrated is another example contact layer 1200 that has an aperture 1202 there through. The deflectable members included in the contact layer 1200 are simply supported beams 1204-1208. The simply supported beams 1204-1208 each comprise a respective flag 1210-1214 (e.g., the simply supported beam 1204 comprises the flag 1210, the simply supported beam 1206 comprises the flag 1212, and the simply supported beam 1208 comprises the flag 1214). The flags 1210-1214 are each respectively located at approximately a center of the corresponding simply supported beam 1204-1208.

In contrast to the examples shown in FIGS. 9-11, the deflectable members of the contact layer 1200 are not cantilevered. When a lead is inserted in the aperture 1202, the lead physically contacts the flags 1210-1214, which causes the simply supported beams 1204-1208 to twist. Thus, the flags 1210-1214 deflect out of a plane when the lead is inserted through the aperture 1202. Moreover, when the lead is inserted in the aperture 1202, electrical connections can be formed between a contact portion of the lead and the flags 1210-1214, and hence, the simply supported beams 1204-1208. Upon the lead being removed from the aperture 1202, the simply supported beams 1204-1208 return to the untwisted state shown in FIG. 12.

Figure 13:
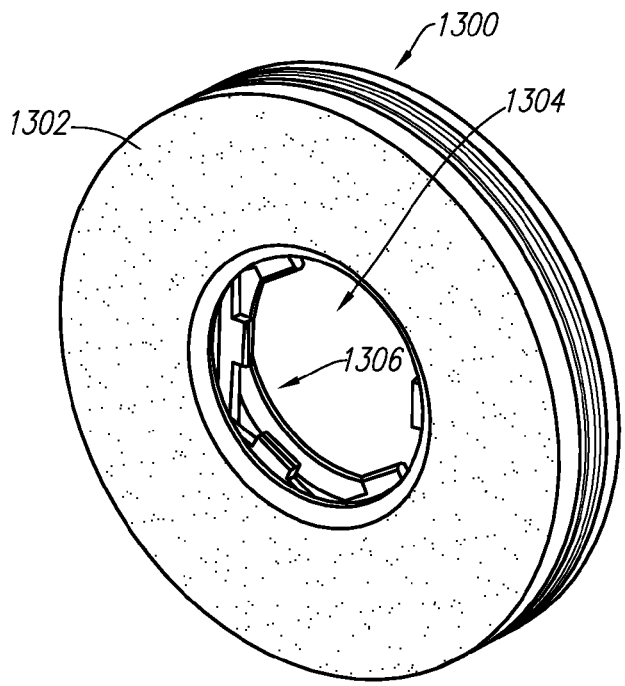
FIGS. 13-14 illustrate isometric views of a contact block that includes contact layers with deflectable members that are simply support beams.
Figure 14:
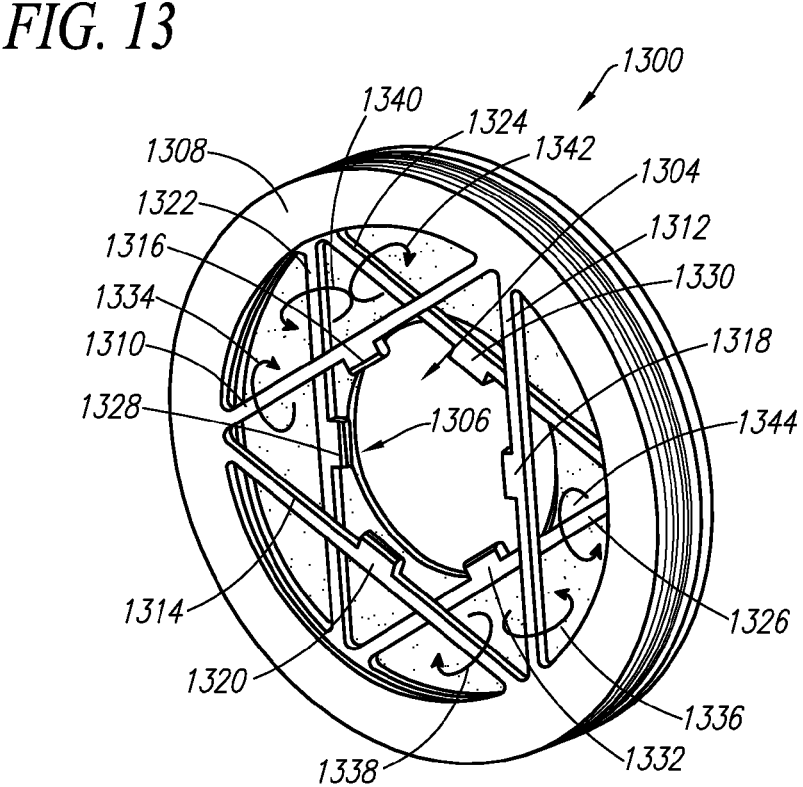

FIGS. 13 and 14 show isometric views of a contact block 1300 that includes contact layers with deflectable members that are simply support beams (e.g., the contact layer 1200 of FIG. 12). FIG. 13 depicts the contact block 1300 including an outer layer 1302, while the outer layer 1302 is removed from the contact block 1300 in FIG. 14 to expose other layers positioned beneath the outer layer 1302 in a stack of layers of the contact block 1300. The contact block 1300 has a bore 1304 there through, which is defined by respectively aligned apertures of the layers of the contact block 1300. Moreover, an arrow 1306 shows a direction of insertion of a lead through the bore 1304.

The contact block 1300 includes two contact layers, namely, a contact layer 1308 and another contact layer positioned beneath the contact layer 1308 in the stack of layers of the contact block 1300. The contact layer 1308 includes simply supported beams 1310-1314, which each comprise a respective flag 1316-1320. Moreover, the other contact layer beneath the contact layer 1308 includes simply supported beams 1322-1326, which each comprise a respective flag 1328-1332. The contact layer 1308 and the other contact layer beneath the contact layer 1308 are rotated with respect to each other such that the flags 1316-1320 and the flags 1328-1332 are offset from each other (e.g., non-overlapping); thus, the flags 1316-1320 do not physically contact the flags 1328-1332, particularly when the lead is inserted through the bore 1304.

When the lead is inserted through the bore 1304 in the direction of the arrow 1306, the lead physically contacts the flags 1316-1320 and 1328-1332, which causes the simply supported beams 1310-1314 and 1322-1326 to respectively twist as shown by arrows 1334-1344. Moreover, when the lead is removed from the bore 1304, the simply supported beams 1310-1314 and 1322-1326 return to the positions shown in FIG. 14.

According to an example, the contact layer 1308 and the other contact layer beneath the contact layer 1308 can be adjacent each other in the contact block 1300 (e.g., not separated by a spacer layer). By way of another example, the contact layer 1308 and the other contact layer beneath the contact layer 1308 can be separated by a spacer layer (not shown) positioned there between.

Figure 15:
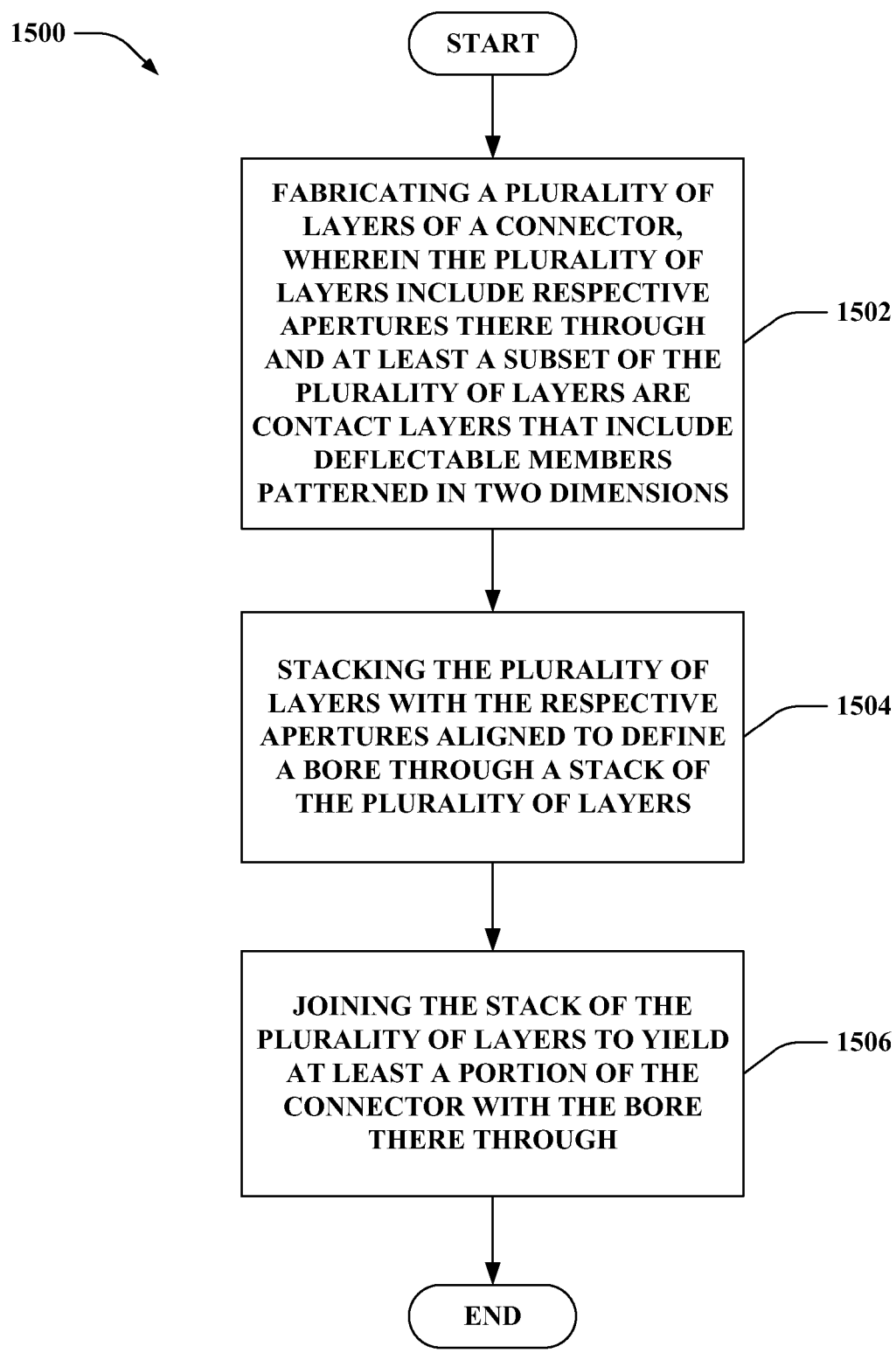
FIG. 15 illustrates a methodology that facilitates manufacturing a connector.

FIG. 15 illustrates a methodology relating to manufacturing a connector that includes a plurality of thin profile stacked layers. While, for purposes of simplicity of explanation, the methodology is shown and described as a series of acts, it is to be understood and appreciated that the methodology is not limited by the order of acts, as some acts can, in accordance with one or more embodiments, occur in different orders and/or concurrently with other acts from that shown and described herein. For example, those skilled in the art will understand and appreciate that a methodology could alternatively be represented as a series of interrelated states or events, such as in a state diagram. Moreover, a subset of the illustrated acts may not be required to implement a methodology in accordance with one or more embodiments.

FIG. 15 illustrates a methodology 1500 that facilitates manufacturing a connector. At 1502, a plurality of layers of a connector can be fabricated. The plurality of layers include respective apertures there through. Moreover, at least a subset of the plurality of layers are contact layers that include deflectable members patterned in two dimensions. According to an example, the plurality of layers can be fabricated by employing wire EDM, laser cutting, or photolithography. The plurality of layers of the connector that are fabricated can additionally include one or more of spacer layer(s), stop layer(s), outer layer(s), and so forth. Further, the plurality of layers can be fabricated in one or more sheets.

Pursuant to an illustration, wire EDM is a manufacturing process whereby a desired shape is obtained using electrical discharges. Thus, through wire EDM, material can be removed from a sheet to form two dimensionally patterned layers of the connector using a series of rapidly recurring discharges between electrodes. According to another illustration, laser cutting can utilize a laser to cut material from a sheet to form two dimensionally patterned layers of the connector. With laser cutting, an output of a laser is directed at the material to be cut, thereby yielding the two dimensionally patterned layers. Pursuant to a further illustration, photolithography can be used to selectively remove material from a sheet to yield the two dimensionally patterned layers. For instance, light can be employed to transfer a pattern to a light sensitive chemical deposited on the sheet, and a series of chemical treatments can engrave the pattern into the sheet underneath the light sensitive chemical. Some examples of photolithography include metal photoetching, electroforming, or thin film/microelectronics techniques. Further, photolithography can efficiently create complicated two dimensional patterns. It is to be appreciated, however, that the foregoing illustrations are provided as examples, and the claimed subject matter is not so limited.

At 1504, the plurality of layers can be stacked with the respective apertures aligned to define a bore through a stack of the plurality of layers. For instance, centers of the respective apertures of the plurality of layers can be aligned to overlap in the stack. By way of example, spacer layers can be positioned adjacent to the contact layers in the stack (e.g., a contact layer can be positioned between and adjacent to two spacer layers), where apertures through the spacer layers provide space for the deflectable members of the contact layers to move. At 1506, the stack of the plurality of layers can be joined to yield at least a portion of the connector with the bore there through. The stack can be joined, for example, mechanically with fasteners, through mechanical upsetting, bending, or folding, with adhesives, through pressure, welding (e.g., resistance welding, etc.), or diffusion bonding, or the like.

Figure 16:
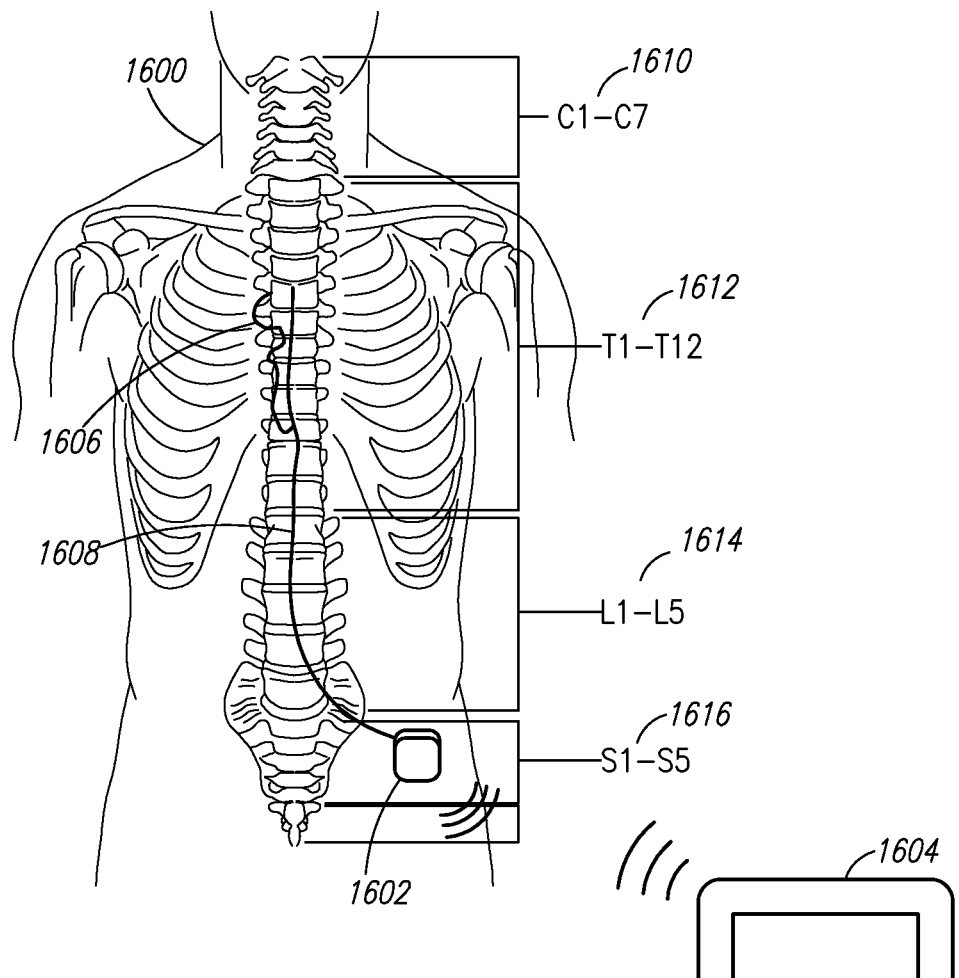
FIG. 16 illustrates an example application of a stimulator system for providing spinal stimulation.

FIG. 16 shows an example application of a stimulator system for providing spinal stimulation. As depicted, an IPG 1602 (e.g., the implantable medical device 100 of FIG. 1) is shown implanted in a patient 1600. Also shown is the human spine comprising the C1-C7 cervical vertebrae 1610, the T1-T12 thoracic vertebrae 1612, the L1-L5 lumbar vertebrae 1614, and the S1-S6 sacral vertebrae 1616. Electrodes 1606 are shown disposed at the distal end of the spine and are positioned near the thoracic vertebrae 1612. Electrodes 1606 are attached to the IPG 1602 via electrode leads 1608.

The leads 1608 and electrodes 1606 may be positioned anywhere along the spine to deliver the intended therapeutic effects of spinal cord electrical stimulation in the desired region of the spine. The distal end of the lead 1608 with its accompanying electrodes 1606 may be located beneath the dura and adjacent a desired portion of the spinal cord using well-established and known techniques for implanting and positioning SCS leads 1608 and electrodes 1606, and the IPG 1602 may be programmed using a clinician or other type of programmer 1604 (such as a patient controller or pocket controller) as desired.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. An electrical connector, comprising:
    a plurality of layers with respective cylindrical apertures therethrough, wherein the plurality of layers are joined in a stack with the respective cylindrical apertures aligned to define a bore through the stack, wherein a lead is receivable in the bore; and
    at least one of the plurality of layers being a contact block comprised of a conductive material that includes a plurality of individual thin deflector layers, wherein each one of said individual thin deflector layers comprises a plurality of integral deflectable members each having an end portion or flag extending into the bore of the contact block from a wall of the cylindrical aperture of the respective deflector layer, wherein the deflectable members end portions or tabs are deflected by the lead such that the deflectable members of all of said individual thin layers of the contact block act in concert to form an electrical connection with a given conductive portion of the lead when the lead is received in the bore.

2. The electrical connector of claim 1, wherein the deflectable members are deflectable in a plane.

3. The electrical connector of claim 1, wherein the deflectable members are deflectable out of a plane.

4. The electrical connector of claim 1, wherein the deflectable members and a remainder of the contact layer are contiguous.

5. The electrical connector of claim 1, wherein the deflectable members are cantilevered beams.

6. The electrical connector of claim 1, wherein the deflectable members are cantilevered spirals.

7. The electrical connector of claim 1, wherein the deflectable members are cantilevered serpentine structures.

8. The electrical connector of claim 1, wherein the deflectable members are simply supported beams that comprise flags.

9. The electrical connector of claim 8, wherein the simply supported beams are twisted by the flags being displaced by the lead when the lead is received in the bore.

10. The electrical connector of claim 1, wherein the deflectable members of the contact layer extend into an aperture through the contact layer.

11. The electrical connector of claim 1, wherein a thickness of the contact layer is less than 0.006 inches.

12. The electrical connector of claim 1, wherein a thickness of the contact layer is less than 0.005 inches.

13. The electrical connector of claim 1, wherein said contact block further comprises at least two spacer layers, wherein at least one of the plurality of deflector layers is positioned between and adjacent to the two spacer layers, and the two spacer layers provide space for the deflectable members of the adjacent deflector layers to move within the respective apertures through the two spacer layers.

14. The electrical connector of claim 1, wherein at least one of the plurality of layers is a stop layer that limits out of plane motion of the deflectable members of a contact layer.

15. The electrical connector of claim 1, wherein at least one of the plurality of layers is an outer layer that makes contact with the lead as it is inserted into the bore to align the lead for insertion.

16. The electrical connector of claim 1, wherein the plurality of layers are made of a conductive material.

17. The electrical connector of claim 16, wherein the conductive material is one of stainless steel, titanium, nickel, chromium, carbon, zirconium, niobium, molybdenum, palladium, hafnium, tantalum, tungsten, iridium, platinum, gold, or an alloy thereof.

18. The electrical connector of claim 1, wherein the contact layer is made of a conductive material and at least one of the plurality of layers other than the contact layer is made of a non-conductive material.

19. The connector of claim 1, wherein said contact block further comprises at least one additional layer provided between two of said individual deflector layers, said one additional layer being comprised of said conductive material without having any of the deflectable members.

20. The connector of claim 1, wherein said contact block further comprises at least one additional layer provided next to at least one of said individual deflector layers, said one additional layer being comprised of said conductive material without having any of the deflectable members and having a cylindrical aperture smaller than apertures formed in the individual deflector layers.

21. A medical system, comprising:
a lead with a proximal end and a distal end, wherein the proximal end includes a plurality of inline contact portions separated by insulator portions, and the distal end at least one of includes, or is coupled to, a plurality of electrodes; and
an implantable medical device, comprising:
a housing that is hermetically sealed to provide an enclosure for at least one of control circuitry, a power supply, or a charging coil; and
a header that includes a connector comprised of a plurality of contact blocks that are electrically connected to the at least one of the control circuitry, the power supply, or the charging coil, wherein the connector defines a bore through the contact blocks in which the lead is receivable to form electrical connections between the contact portions of the lead and the contact blocks, the contact blocks each include a plurality of stacked and joined layers with respective cylindrical apertures there through to define the bore, and at least a plurality of the stacked and joined layers of each of the contact blocks being a conductive contact layer that includes integral deflectable members each having an end portion or flag extending from a wall of the cylindrical aperture of the conductive contact layer into the bore that is deflected by the lead and forms electrical connections with the contact portions of a pin on the lead when the lead is received in the bore such that for each contact portion of the pin, a plurality of layers that include integral deflectable members are arranged, each separated by at least one conductive layer not comprising deflectable members, for working in concert for contacting any given contact portion.

22. The medical system of claim 21, wherein the implantable medical device is an Implanted Pulse Generator (IPG).

23. The medical system of claim 21, wherein the deflectable members are at least one of cantilevered beams, cantilevered spirals, cantilevered serpentine structures, or simply supported beams that comprise flags.

24. The medical system of claim 21, wherein the plurality of stacked and joined layers of each of the contact blocks is made of a conductive material.

25. The medical system of claim 24, wherein the conductive material is one of stainless steel, titanium, nickel, chromium, carbon, zirconium, niobium, molybdenum, palladium, hafnium, tantalum, tungsten, iridium, platinum, gold, or an alloy thereof.

26. The medical system of claim 21, wherein the plurality of contact blocks are separated by seals.

27. The medical system of claim 21, wherein contact layers from the plurality of stacked and joined layers are made of a conductive material, and at least a subset of other layers from the plurality of stacked and joined layers are made of a non-conductive material.

28. A method of manufacturing, comprising:
fabricating a plurality of layers of a connector, wherein the plurality of layers include respective cylindrical apertures there through and at least a subset of the plurality of layers are conductive contact layers that include a plurality of deflector layers each having integral deflectable members patterned in two dimensions, said deflectable members each having an end portion or flag extending into a bore formed by the apertures from a wall of the apertures of the contact layer;
stacking the plurality of layers with the respective apertures aligned to define the bore through a stack of the plurality of layers such that a plurality of deflector layers are stacked and arranged in concert to contact a common conductive contact portion on a pin; and
joining the stack of the plurality of layers to yield at least a portion of the connector with the bore there through.

29. The method of claim 28, further comprising fabricating the plurality of layers of the connector via employing at least one of wire electric discharge machining (EDM), laser cutting, or photolithography.

30. The method of claim 28, wherein the plurality of layers that are fabricated further include one or more of stop layers, outer layers, or spacer layers.

31. The method of claim 28, wherein each of the contact layers are stacked between and adjacent to two spacer layers.

32. The method of claim 28, further comprising joining the stack of the plurality of layers at least one of mechanically, with adhesives, or through bonding.

33. The connector of claim 28, wherein each adjacent pair of said plurality of deflector layers are stacked and arranged in concert with at least one additional conductor layer provided there between, each of the additional conductive layers having a cylindrical aperture without integral deflectable members.

34. An electrical connector, comprising:
a plurality of contact blocks each associated with a respective contact portion of a pin and having a bore therethrough, wherein said contact blocks are separated from each other by an insulating component and wherein each contact block is comprised of:

a plurality of deflector layers, each deflector layer being comprised of a conductive material that includes a plurality of integral deflectable members each having an end portion or flag extending into a bore of the deflector layer, wherein the deflectable members end portions or tabs are deflected by the pin such that the deflectable members of all of said deflector layers of the contact block act in concert to form an electrical connection with the associated contact portion of the pin when the pin is received in the bore, and at least one separator layer, each separator layer being configured without deflectable members and having a bore to receive the associated contact portion of the pin.

* * * * *